(12) United States Patent
Kuhlmann et al.

(10) Patent No.: US 7,068,803 B2
(45) Date of Patent: Jun. 27, 2006

(54) ACOUSTIC DEVICE WITH MEANS FOR BEING SECURED IN A HUMAN EAR

(75) Inventors: Peer Kuhlmann, Hvidovre (DK); Jorgen M. Lundbeck, Skovlunde (DK)

(73) Assignee: NEXTLINK.TO A/S, Gentofte (DK)

( * ) Notice: Subject to any disclaimer, the term of this patent is extended or adjusted under 35 U.S.C. 154(b) by 0 days.

(21) Appl. No.: 10/451,099

(22) PCT Filed: Dec. 21, 2001

(86) PCT No.: PCT/DK01/00861

§ 371 (c)(1),
(2), (4) Date: Dec. 30, 2003

(87) PCT Pub. No.: WO02/52890

PCT Pub. Date: Apr. 7, 2002

(65) Prior Publication Data

US 2004/0096075 A1    May 20, 2004

(30) Foreign Application Priority Data

Dec. 22, 2000  (DK) ................. 2000 01927
Feb. 26, 2001  (DK) ................. 2001 00320

(51) Int. Cl.
*H04R 25/00* (2006.01)
(52) U.S. Cl. ............ 381/328; 381/315; 381/322
(58) Field of Classification Search ........... 381/71.6, 381/72, 23.1, 312, 315, 322, 328, 329, 330
See application file for complete search history.

(56) References Cited

U.S. PATENT DOCUMENTS

| | | | |
|---|---|---|---|
| 931,768 A | 8/1909 | Kirkpatrick | |
| 3,470,328 A * | 9/1969 | Daniels | 381/322 |
| 4,587,965 A | 5/1986 | De Boer et al. | |
| 4,878,560 A | 11/1989 | Scott | |
| 5,048,090 A | 9/1991 | Geers | |
| 5,333,622 A | 8/1994 | Casali et al. | |
| 5,412,736 A | 5/1995 | Keliiliki | |
| 5,659,156 A | 8/1997 | Mauney et al. | |
| 5,659,620 A | 8/1997 | Kuhlman | |
| 5,677,964 A | 10/1997 | Sun | |
| 5,721,783 A * | 2/1998 | Anderson | 381/328 |
| 6,094,492 A * | 7/2000 | Boesen | 381/312 |
| 6,122,388 A | 9/2000 | Feldman | |

FOREIGN PATENT DOCUMENTS

| | | |
|---|---|---|
| DE | 297 18 483 U 1 | 4/1999 |
| DE | 200 09 908 U 1 | 10/2000 |
| EP | 0 637 896 A2 | 2/1995 |
| EP | 0 952 756 A2 | 10/1999 |

* cited by examiner

*Primary Examiner*—Sinh Tran
*Assistant Examiner*—Brian Ensey
(74) *Attorney, Agent, or Firm*—Oliff & Berridge, PLC

(57) ABSTRACT

A device with acoustic effect and a housing for being located in the cavum conchae of a human ear. The housing has a face adapted for abutment on the tragus, a face adapted for abutment on the antitragus, a mouthpiece adapted for being inserted into the mouthing of the auditory tract. A resilient means is adapted to abutment on the cartilage arch between the antihelix and the concha and influences the housing by a force oriented forwards towards the tragus. The resilient means is a leaf spring with a spring rigidity that decreases with the distance from the housing, whereby a uniform distribution of the force towards the cartilage arch at the concha is provided. The device may be a passive noise shield or it may have on eor two transducers for one-way or two way communication.

31 Claims, 4 Drawing Sheets

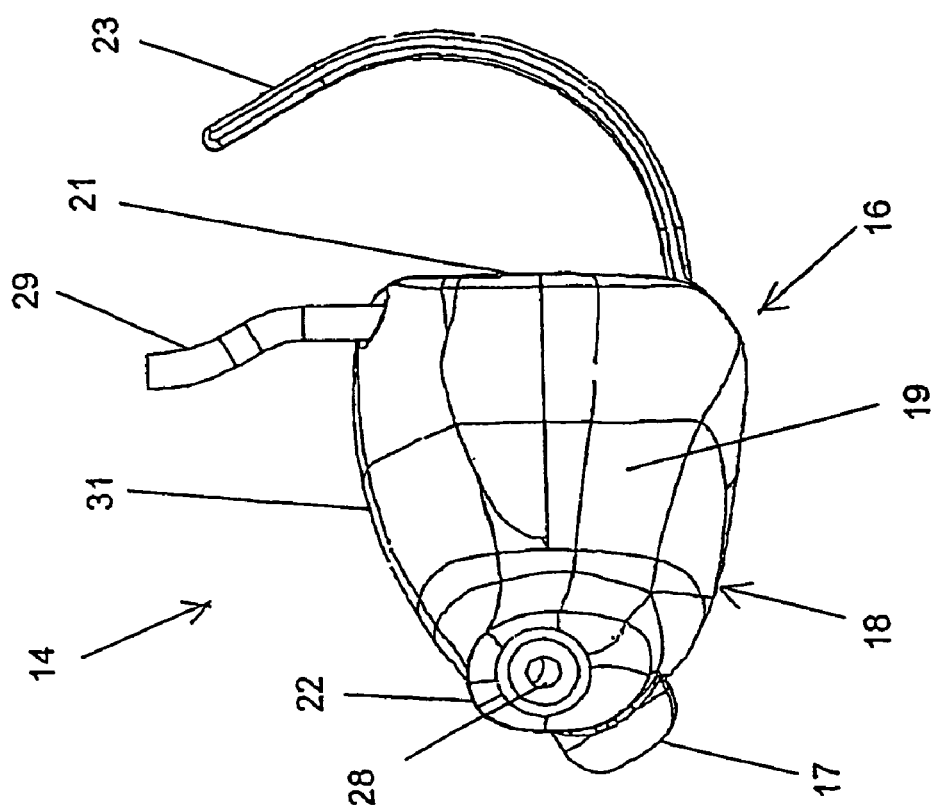
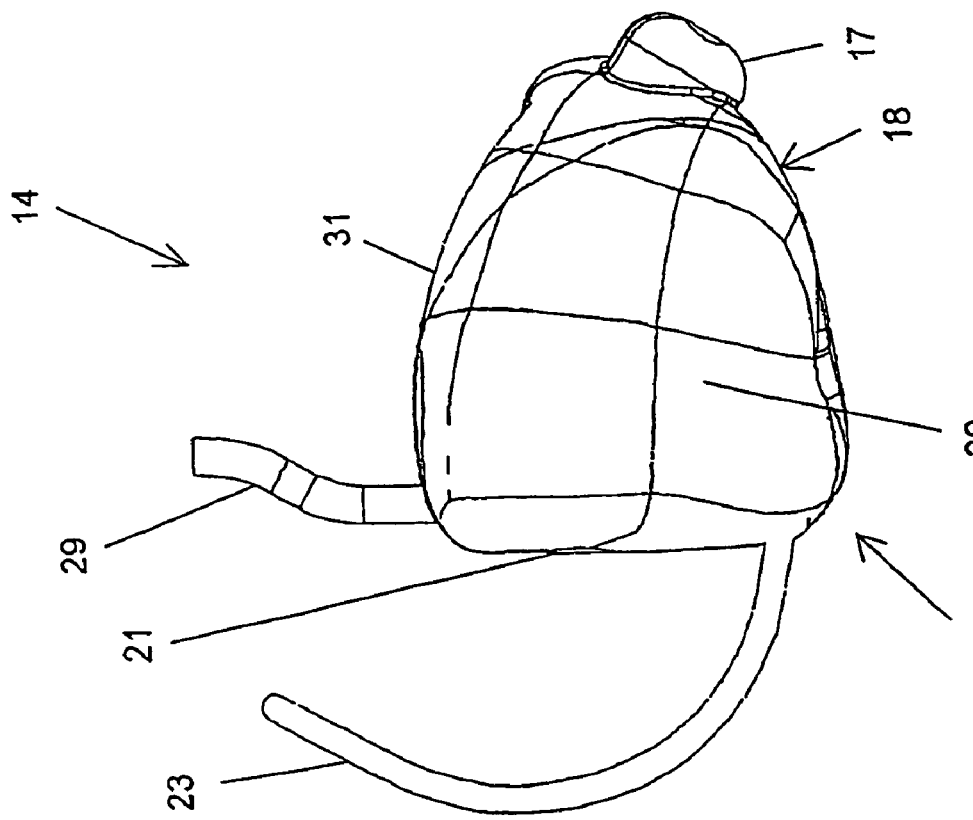

1. Helix
2. Meatus acusticus externus
3. Anthelix
4. Crus superius anthelicis
5. Crus inferius anthelicis
6. Fossa triangularis
7. Tragus
8. Radix helicis
9. Cimba conchae
10. Cavum conchae
11. Antitragus
12. Lobulus
13. Meatus

ACOUSTIC DEVICE WITH MEANS FOR BEING SECURED IN A HUMAN EAR

This invention relates to an acoustic device for being arranged in the outer ear of a human being, and in particular an ear-plug with an electro-acoustic transducer and a personal shield against noise and a headset or earpiece for cord- or cordless communication.

By an acoustic device is intended a device with an acoustic effect or function. By an electro-acoustic transducer is, in this context, to be understood a sound emitter or a microphone. The term 'headset' as used herein is intended to designate a device that is worn on a user's head and that comprises both a sound emitter and a microphone, whereby the user is able to perform two-way communication. The term 'headpiece' is to be understood as such device as has dimensions that make it suitable for being arranged on or in the outer ear of a user.

As a personal shield against noise plugs are conventionally used for insertion into the external auditory canal or arched shields for being arranged around the outer ear.

Shields provide adequate attenuation of noise, but they may be undesirable due to their making the use of other personal equipment, such as glasses or protecting helmets, more difficult or impossible. They are comparatively heavy and they prevent ventilation, etc.

Ear-plugs for arrangement in the auditory canal are associated with other drawbacks, such as having a propensity to working their way out, provoking pressure within the auditory canal, being difficult to arrange satisfactorily, etc.

One particular condition in the context of noise protective means is the balance between conflicting considerations: on the one hand it is desired to protect against noise, on the other hand it is desired to be able to communicate and to orient oneself acoustically.

U.S. Pat. No. 4,878,650 teaches a dish-shaped earplug having a shape that is adapted to the cavum conchae of the outer ear. The earplug is made of an elastic material, and it is 2–5% larger than the cavum conchae, whereby an elastic force is exerted that presses the plug against the rim of the concha.

U.S. Pat. No. 931,768 discloses a noise shield in the form of a plate element for covering the concha. A resilient thread is integrated along the edge for exerting a resilient force for ensuring close abutment on the rim of the concha.

U.S. Pat. No. 5,048,090 relates to a hearing aid featuring an elastic brace for resilient abutment on the rear rim of the concha for exerting a pressure on that part of the hearing aid that extends into the auditory canal.

DE 29,718,483 U1 relates to 'otological apparatuses' in general. In a manner similar to the one taught in the above-referenced U.S. Pat. No. 5,048,090 a C-shaped brace is used in this disclosure for resilient abutment on the rear rim of the concha and for exerting a pressure on the apparatus to secure it in the auditory canal.

U.S. Pat. No. 5,333,622 teaches a moulded ear-plug that is moulded for the individual user. This ear-plug may comprise a resonator for modifying the sound and change its character.

U.S. Pat. No. 4,587,965 teaches an ear-plug with a canal wherein a sound-attenuating filter can be inserted.

An ear-plug with an electro-acoustic sound emitter or loudspeaker is known in a variety of configurations that are distinctive with regard to their use and with regard to the way in which they are adapted to the human ear. Relevant uses include devices for listening to music, aids for users with hearing impediments and devices intended for communication.

U.S. Pat. No. 5,659,620 teaches a plug for being arranged in the outer ear, wherein no particular means are provided for securing the plug. This document also teaches a microphone in combination with the earplug with the object of being able to capture speech by the vibrations that expand from the mouth cavity through the jawbone and to the outer ear, more specifically to the bottom of the auditory canal at the tragus.

DE 3,831,207 teaches a headset with an earplug and a microphone that is carried by a brace intended for being suspended above the outer ear.

WO 97/27721 also teaches a communication device with brace for suspension above the ear.

DE 4,116,533 shows a sound emitter for being located in the ear wherein a device is present for attachment around the earlobe.

DE 4,135,286 shows a device intended for forming a casting of the outer ear of a patient with the object of subsequently being able to configure an earplug for a hearing aid that thereby achieves an individual fitting.

EP 673,587 shows an ear microphone for being located in the outer ear of a user in contact with the tragus, wherein the speech signals of the user are captured.

The known devices have various drawbacks. Individual adaptation of an earplug is a slow and cumbersome process that is costly to realise. A brace behind the outer ear or a device for being clamped on the outer ear may constitute a nuisance and can be completely out of the question in combination with other equipment, such as glasses, noise shields, protective helmets or the like. Earplugs that do not feature particular devices for attachment and that are not fitted individually are not properly secured and therefore easily lost, which may exclude the use of that kind of ear plugs from being used for other ends than objects and environments that are not critical in any way.

Besides, earplugs are known wherein a cap is provided of a soft material, such as rubber foam, around a hard core with the object of providing improved adaptation and attachment. In use, the soft material, eg foamed rubber is, however, exposed to soiling with dust or earwax. Foamed rubber is not very easily cleaned and it can therefore easily become unhygienic.

With a device according to the invention an improved adaptation to the human ear is accomplished over a wide range of sizes and shapes, improved attachment of the earplug is accomplished, improved transmission of acoustic signals to and from the earplug is accomplished, and improved shielding against external noise is obtained.

According to convenient embodiments the spring is configured so as to distribute the force along the cartilage arch between antihelix and concha, more specifically around cymba conchae and cavum conchae, whereby punctiform influences are evened out thereby providing improved comfort.

This can be accomplished by configuring the spring as a leaf spring that brings about, on the one hand, the spring effect and, on the other hand, brings about an elongate contact element.

Conveniently the leaf spring has a spring rigidity that decreases, eg linearly, with the distance from the housing of the earplug, whereby a uniform distribution of the force against the cartilage arch around the concha is provided. This yields the most even distribution of the impact. The leaf spring can conveniently have a larger curvature at its free end than at the housing of the earplug, whereby it is avoided that the free end of the leaf spring exerts a punctiform pressure against the user's ear.

The housing may comprise an integral unit for electrical amplification and signal processing, whereby a convenient integral unit is obtained that presents the option of adaptation of an electro-acoustical signal and provides adequate suppression of electrical noise.

The spring may comprise an integral electrical conductor, thereby enabling it to be used as radio antenna.

Conveniently the earplug comprises a microphone, preferably a microphone configured for abutment in the outer ear at the tragus with a view to capturing speech transmitted through conduction of vibrations from the mouth region and through the jawbone and soft tissue. Hereby it is possible to capture speech signals from the user, also in environments with heavy noise. In particular, it is now possible to use the earplug in an intercom for a person who simultaneously wears a noise shield.

As a variety the earplug may comprise a microphone mounted on an arm in accordance with the principle shown in DE 3,831,207 or on the outside of the plug.

According to a further aspect of the invention a headset for cordless communication is provided.

Hereby a very compact headset or earpiece is provided for cordless communication that can be manufactured inexpensively, that provides adequate fitting and does not give rise to nuisances in connection with the use of other equipment, eg noise shield or protective helmet.

In the following, preferred embodiments of the invention will be described with reference to the drawing, in which FIG. 1 shows a lateral view of an earplug from its distal side and with the spring compressed;

FIG. 2 shows a depiction of the earplug shown in FIG. 1, seen from its proximal side;

Figure 3:
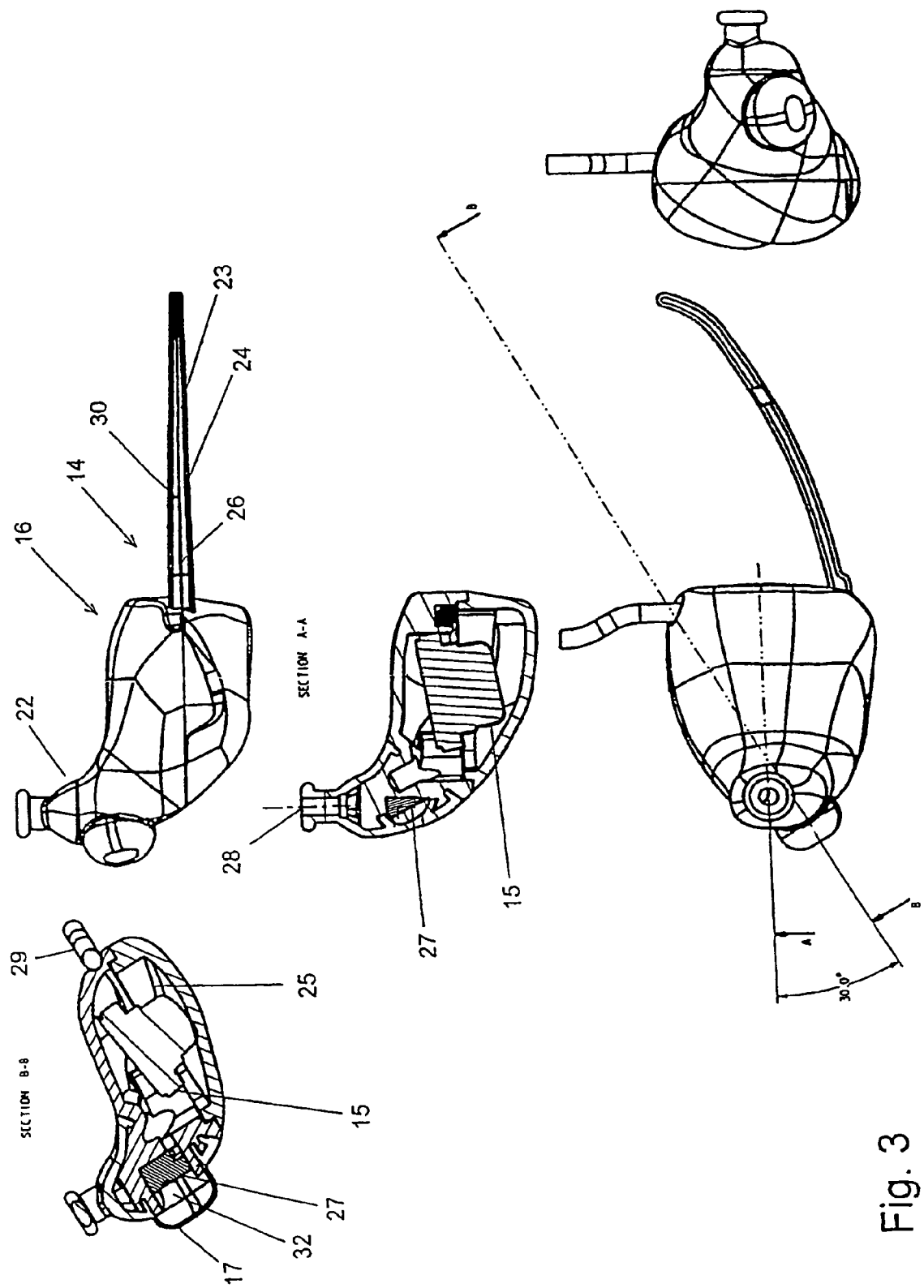
FIG. 3 shows the earplug according to the invention with the spring in unbiased state and in a depiction from three different angles and in two sectional views.

The figures are schematical and therefore only show such details that are relevant for the person skilled in the art to exercise the invention, whereas—for the sake of overview—other details have been omitted. Everywhere the same reference numerals are used to designate identical or corresponding parts.

Expressions that denote orientation or a direction, such as upwards, downwards, front and rear, are—unless shown to the contrary—to be understood in relation to a person who wears the earplug in its position of use in his ear. By the 'proximal or medial face of the earplug' is to be understood the face that faces towards the median plane of the person who wears the earplug in his ear, and by the 'distal or lateral face of the earplug' is to be understood the face of the earplug that faces away from the median plane of that person.

FIGS. 1 and 2 show an earplug 14 according to the invention, seen from the distal face 20 and the proximal face 19, respectively. The earplug 14 essentially comprises a housing 16 and a spring 23. The figures also show a part of a cord 29 intended for exchange of electrical signals with an external electrical signal-processing unit.

The earplug 14 comprises a mouthpiece 22 with a sound channel 28 and configured for approximately sealing contact with the mouthing of the auditory canal (meatus). Also shown is a protrusion with a contact cushion 17 intended for abutment against the auditory canal at the tragus close to the jawbone.

The housing 16 is delimited downwardly essentially by the antitragus-face 18, by the rear face 21 and by the top face 31.

FIG. 3 shows the same details as FIGS. 1 and 2, the spring being, however, shown in relieved state therein. In sectional views, in particular some of the internal details of the earplug are shown, including the sound emitter 15 and the microphone 27. Examples of a suitable microphone include an electret microphone model 9721 manufactured by the company Microtronic A/S in Denmark. The microphone may comprise the technology that is taught in U.S. Pat. No. 5,255,246. Other microphones may also be used, provided they have similar dimensions and sensitivity.

Preferably a microphone is used that has good sensitivity to vibrations, but low sensitivity to airborne sound in order to ensure that the best possible immunity is obtained against external noise.

As sound emitter or loudspeaker it is possible to use eg a unit designated Receiver Series 1900 from the company Microtronic A/S in Denmark. Other types of loudspeakers with suitable magnitudes and acoustic properties can also be used. The loudspeaker is mounted within the housing and an acoustic canal 28 is provided towards the mouthpiece 22, thereby providing good transmission of the sound signal to the auditory canal of the user.

Besides, the housing contains an electrical signal-processing unit 25. According to one embodiment this unit comprises electrical devices for amplification and signal processing and for transmission through the cord 29 to an external unit. According to a further embodiment (not shown specifically) the cord 29 is omitted and in the signal-processing unit 25 an electrical radio transmitter and radio receiver are provided in connection with an antenna 26 integral with the spring 23. The radio transmitter and receiver may be eg a unit configured for communication in accordance with the Bluetooth protocol. Alternatively it may be a unit configured for communication in accordance with the DECT protocol (Digital European Cordless Telephone) or some other protocol for cordless transmission.

The housing may be moulded in ABS plastics, eg Novodur from Bayer. The mouthpiece 22 may comprise rubber of a soft type for improved comfort, eg fluoro-rubber type FPM from Codan Rubber A/S in Denmark.

Furthermore, FIG. 3 shows the spring 23. The spring comprises a core 30 of resilient plastics, eg polyacetal or polyoxymethylene (POM). The spring core may have a thickness of 1.1 mm. The width may vary from 2.6 at the bottom part close to the housing and to as little as 1.8 at the outermost end. By this tapering such spring rigidity is obtained as decreases with its distance from the housing, whereby an even distribution of the force in the arrangement is obtained in its abutment on the ear. Owing to its dimensions the spring is more rigid in its transversal plane, eg four to five times more rigid, whereby the spring is caused to act as a leaf spring, ie it preferably flexes in one plane. It will also appear that the outermost part of the spring has, in its unloaded state, a larger curvature than the remainder of the spring. Hereby it is avoided that the outermost tip of the spring exerts a punctiform pressure on the ear of the user, which might be painful to the user.

According to the preferred embodiment there is, around the spring core 30, mounted a tubular member 24 of soft material, eg of a wall thickness of from 0.4 to 0.8 mm. A tubular member of polysiloxane or silicon rubber from the company Asicomo A/S in Denmark has been found to be suitable. Other similar materials could also be used. The tubular member provides improved user comfort. Further, it is possible to have individual adaptation in a very simple and lowcost manner, quite simply by replacing the silicon hose with another one with a different wall thickness.

The spring may have an integral electrical conductor that it is able to use as radio antenna. This may be realised, eg by a thin electrical conductor 26 being cast therein.

The microphone 27 is mounted in the housing, whereby it is sealingly encapsulated and delimited relative to the auditory canal 28. The sound-sensitive side of the microphone faces towards the pressure chamber 32 that is upwardly covered by that part of the housing that forms the tragus-face 17 or the contact cushion. Hereby the optimal transmission of sound from the auditory canal at the tragus and the optimal suppression of external noise are obtained.

According to an alternative embodiment (not shown) the earplug is configured as an ordinary acoustic microphone mounted on an arm, eg as shown in 38 31 207 or on the housing of the plug.

Figure 4:
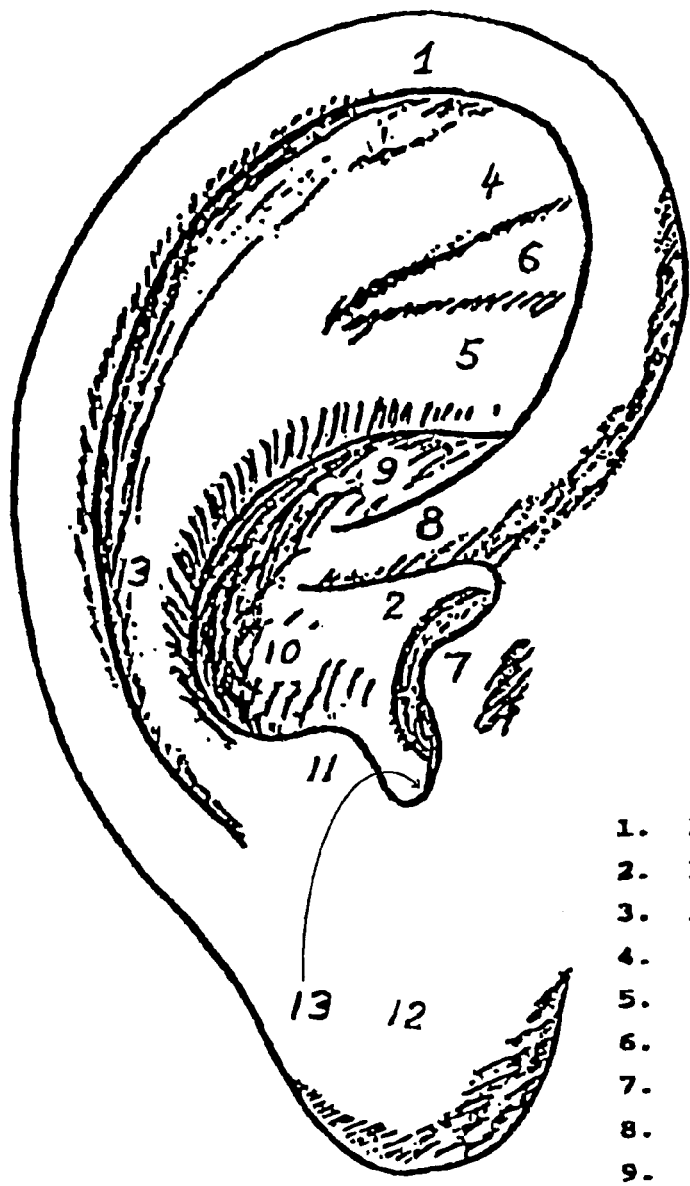
FIG. 4 is a lateral view of a human ear with the Latin designations of its various parts.

Reference is now made to FIG. 4 for a description of the human ear with the designations in Latin as follows:
1) Helix
2) Meatus acusticus externus
3) Antihelix
4) Crus superius anthelicis
5) Crus inferius antehelicis
6) Fossa triangularis
7) Tragus
8) Radix helicis
9) Cymba conchae
10) Cavum conchae
11) Antitragus
12) Lobulus
13) Meatus The earplug according to the invention is inserted, as will be understood, in cavum conchae 10, partially behind the tragus 7 and the antitragus 11, the spring supporting against the cartilage fold between antihelix 3 and cymba conchae 9 in extension of cavum conchae 10.

Figure 5:
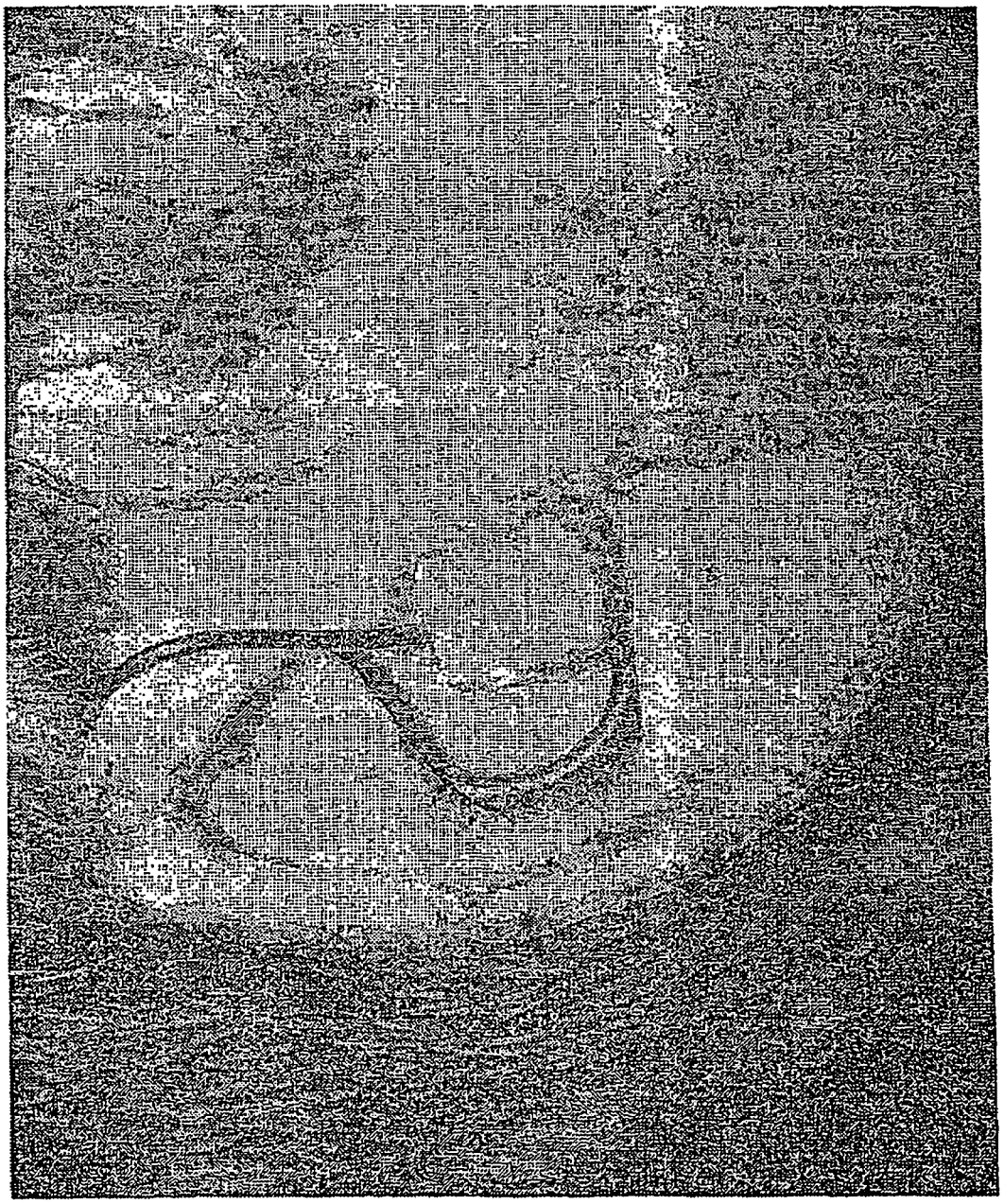
FIG. 5 is a photo of an earplug according to the invention, arranged in its position of use in a human ear.

FIG. 5 shows photo of the earplug inserted in a human ear. From this it will appear how the earplug becomes partially concealed underneath the tragus and antitragus, and how the end of the spring becomes partially concealed below the cartilage fold around the concha. It will be understood from the photography how the plug according to the invention achieves good attachment relative to the ear.

FIG. 5 also shows how the cord is located to leave the house at the top and such that it can be conveyed up above and behind the outer ear. This provides the most comfortable location and it simultaneously contributes to keeping the earplug in place.

Herein is shown and described an earplug with one or two electroacoustic transducers for one-way or two-way communication. A correspondingly configured earplug is also suitable for personal noise shield with the option of communication. For exclusive use as noise shield it is an option to omit the transducers altogether.

In its embodiment as noise shield the auditory canal is in communication with one or more openings, which are not shown in further detail herein, in another area of the earplug with the aim of providing pressure equalisation from the auditory duct and towards the surroundings. The canal has a suitably narrow cross section to prevent it from short-circuiting the desired sound insulating effect.

According to one embodiment the canal is provided with particular sound-attenuating measures in the form of a filter or bends of the canal to yield a labyrinth effect for attenuating noise. According to a particular embodiment the sound-attenuation is adjustable, eg by regulation of the cross-section of the canal or by insertion of exchangeable filters.

According to a preferred embodiment sound-attenuating filters are used that are configured such that they are open to sound in the speech-frequency area, but attenuating with respect to sound in other frequency areas. Hereby protection against noise is obtained, while simultaneously the wearer of the earplugs still has the option of acoustic communication. Suitable filters may for instance be obtained from the company Dreve-Otoplastik GmbH, Unna, Germany, under the designations DL-filter 10, DL-filter 20 and DL-filter 30.

The housing may have a shell moulded in ABS plastics, eg Novodur from Bayer. The mouthpiece 22 may comprise a softer type of rubber for improved comfort, eg fluoro-rubber type FPM from Codan Gummi A/S in Denmark. The housing may be filled with sound attenuating material, such as felt.

The spring may be exchangeable, thereby enabling selection of a spring with another length or having another spring rigidity for improved individual customisation.

The length of the housing from the tragus face 17 and to the rear face 21 is, in the preferred embodiment, 22 mm, whereas the height is 17 mm. In case of an unloaded spring the distance from the tragus face and to the end of the spring is 47 mm. The spring is very flexible and can be compressed, eg as much as to a distance of 30 mm from the tragus face. Preferred values for the abutment force within the ear is from 0.8 to 1.5 N and eg from 1 to 1.3 N.

The invention claimed is:

1. An acoustic device for being arranged in a human ear and comprising a housing configured for being located in the outer ear, and forming a closed-ear configuration in the cavum conchae, with a face adapted for abutment on the tragus, a face adapted for abutment on the antitragus, a mouthpiece adapted for being inserted into the mouthing of the auditory tract and a resilient means adapted for abutment on the cartilage arch between the antihelix and the concha and configured for influencing the housing with a force oriented generally forwards towards the tragus, wherein the resilient means comprises an elongated element that distributes the force along the cartilage arch at the concha, and that is mounted approximately tangentially relative to that face of the housing that is configured for contact with the antitragus;
wherein the elongated element is a spring that has a spring rigidity that decreases with the distance from the housing, whereby a uniform distribution of the force towards the cartilage arch is provided at the concha.

2. A device according to claim 1, wherein the spring has such span width that it is able to ensure a resilient tightening of the housing to persons to whom the distance from the mouthing of the meatus to the interior arch within the concha is comprised within the range of from 30 to 50 mm and in particular within the range of from 35 to 45 mm.

3. A device according to claim 1, wherein the spring comprises a leaf spring, whose width decreases with its distance from the housing.

4. A device according to claim 3, wherein the leaf spring has, at its free end, a portion with a larger curvature than at its base.

5. A device according to claim 1, wherein device further comprises an electro-acoustic transducer.

6. A device according to claim 5, wherein the housing comprise an integral unit for electrical amplification and signal-processing of signals to or from the transducer.

7. A device according to claim 1, wherein the spring has an integral electrical conductor, thereby enabling it to be used as antenna for radio-frequency signals.

8. A device according to claim 7, wherein said device further comprises a device for cordless communication.

9. A device according to claim 5, wherein the electro-acoustic transducer comprises a loudspeaker configured for transmitting sound to the mouthpiece.

10. A device according to claim 1, wherein said device further comprises a microphone.

11. A device according to claim 10, wherein the microphone comprises a contact cushion configured for being located in abutment on the auditory tract at the tragus and for capturing vibrations with a view to capturing speech transmitted through transmission of vibrations from the mouth region and through the jawbone.

12. A device according to claim 1, wherein the body comprises an acoustic canal configured for establishing pressure equalisation between the auditory canal and the surroundings.

13. A device according to claim 12, wherein the acoustic canal comprises means for regulating the spreading of sound therethrough.

14. A device according to claim 12, wherein the acoustic canal comprises bends for bringing about a labyrinth effect.

15. A device according to claim 12, wherein the acoustic canal comprises an exchangeable filter.

16. A device according to claim 12, wherein the acoustic canal comprises a filter that is configured for being open to sound in the speech frequency area, but attenuating to sound within other frequency areas.

17. An acoustic device for being arranged in a human ear and comprising a housing configured for being located in the outer ear, in the cavum conchae, with a face adapted for abutment on the tragus, a face adapted for abutment on the antitragus, a mouthpiece adapted for being inserted into the mouthing of the auditory tract and a resilient means adapted for abutment on the cartilage arch between the antihelix and the concha and configured for influencing the housing with a force oriented generally forwards towards the tragus, wherein the resilient means comprises an elongated element that distributes the force along the cartilage arch at the concha, and that is mounted approximately tangentially relative to that face of the housing that is configured for contact with the antitragus;

wherein the elongated element is a spring that has a spring rigidity that decreases with the distance from the housing, whereby a uniform distribution of the force towards the cartilage arch is provided at the concha, and wherein said device further comprises an electro-acoustic transducer.

18. A device according to claim 17, wherein the spring has such span width that it is able to ensure a resilient tightening of the housing to persons to whom the distance from the mouthing of the meatus to the interior arch within the concha is comprised within the range of from 30 to 50 mm and in particular within the range of from 35 to 45 mm.

19. A device according to claim 17, wherein the spring comprises a leaf spring, whose width decreases with its distance from the housing.

20. A device according to claim 19, wherein the leaf spring has, at its free end, a portion with a larger curvature than at its base.

21. A device according to claim 17, wherein the housing comprise an integral unit for electrical amplification and signal-processing of signals to or from the transducer.

22. A device according to claim 17, wherein the spring has an integral electrical conductor, thereby enabling it to be used as antenna for radio-frequency signals.

23. A device according to claim 22, wherein said device further comprises a device for cordless communication.

24. A device according to claim 17, wherein the electro-acoustic transducer comprises a loudspeaker configured for transmitting sound to the mouthpiece.

25. A device according to claim 17, wherein said device further comprises a microphone.

26. A device according to claim 25, wherein the microphone comprises a contact cushion configured for being located in abutment on the auditory tract at the tragus and for capturing vibrations with a view to capturing speech transmitted through transmission of vibrations from the mouth region and through the jawbone.

27. A device according to claim 17, wherein the body comprises an acoustic canal configured for establishing pressure equalisation between the auditory canal and the surroundings.

28. A device according to claim 27, wherein the acoustic canal comprises means for regulating the spreading of sound therethrough.

29. A device according to claim 27, wherein the acoustic canal comprises bends for bringing about a labyrinth effect.

30. A device according to claim 27, wherein the acoustic canal comprises an exchangeable filter.

31. A device according to claim 27, wherein the acoustic canal comprises a filter that is configured for being open to sound in the speech frequency area, but attenuating to sound within other frequency areas.

* * * * *